United States Patent [19]

Khalil et al.

[11] Patent Number: 4,533,691
[45] Date of Patent: Aug. 6, 1985

[54] CHLORINE DIOXIDE ANTIMICROBIAL AGENT FOR LATEX

[75] Inventors: Hamdy Khalil; Orest N. Chick, both of Sarnia, Canada

[73] Assignee: Polysar Limited, Sarnia, Canada

[21] Appl. No.: 560,226

[22] Filed: Dec. 12, 1983

[51] Int. Cl.$^3$ .............................................. C08K 3/16
[52] U.S. Cl. .................................................... 524/401
[58] Field of Search ........................................ 524/401

[56] References Cited

U.S. PATENT DOCUMENTS 3,092,598  6/1963  Hahn et al. .................... 260/29.6
3,303,153  2/1967  Jablonski et al. ............... 260/29.6

Primary Examiner—Harold D. Anderson
Attorney, Agent, or Firm—Stevens, Davis, Miller & Mosher

[57] ABSTRACT

An improved method is provided for inhibiting the growth of microorganisms in a latex comprising homopolymers of $C_{4-6}$ conjugated diolefins, acrylic polymers, vinyl acetate polymers, chloroprene polymers, vinyl pyridine polymers, homopolymers of vinylidene monoaromatic monomers, copolymers of ethylene and propylene, copolymers of acrylonitrile and butadiene or copolymers of butadiene and styrene, copolymers of butadiene and styrene containing one or more monomers selected from the group alpha-beta ethylenically unsaturated aldehydes, alpha-beta ethylenically unsaturated carboxylic acids, amide derivatives of alpha-beta ethylenically unsaturated acids which may be unsubstituted or substituted at the nitrogen atom by a $C_{1-8}$ alkyl or a $C_{1-4}$ alkanol radical, or a $C_{1-8}$ alkyl ester of an alpha-beta ethylenically unsaturated carboxylic acids, said process comprising admixing with said latex a chlorine dioxide gas, aqueous solutions of chlorine dioxide, and two or more chemical compounds which react upon mixing to form chlorine dioxide, in an amount sufficient to generate from 0.001 to 1 parts by weight of chlorine dioxide per 100 parts by weight of polymer in the latex. Such latices are useful in conventional applications such as coatings, and binders.

17 Claims, No Drawings

CHLORINE DIOXIDE ANTIMICROBIAL AGENT FOR LATEX

This invention relates to a method for inhibiting the growth of microorganisms in aqueous latexes comprising one or more synthetic polymers.

Almost all aqueous organic systems, including latexes of synthetic polymers, are subject to contamination and deterioration by microorganisms. The microorganisms grow and proliferate in the aqueous system and produce a variety of undesirable effects. These include the development of offensive odours, coagulation of dispersions, breaking of emulsions, turbidity, changes in pH, changes in viscosity, and slime formation. These effects will at best make the product unpleasant to use and at worst make the product totally unusable from a technical point of view.

In order to protect aqueous organic systems from the effects of microorganisms, a variety of compounds have been developed in the art. When added to the aqueous organic system, these compounds destroy any microorganisms which may be contained therein and which may subsequently come in contact with the aqueous system or at the very least prevent the further extensive proliferation of the microorganisms. These compounds have been referred to by a variety of use-oriented terms including antibiotics, preservatives, disinfectants, antiseptics, antifoulants, bacteriacides, fungicides, mildewcides, slimicides, algaecides, biocides, and antimicrobial agents. The term "antimicrobial agent" will be used hereinafter in referring to these compounds.

It has long been known that aqueous latexes comprising one or more synthetic polymers are susceptible to contamination by microorganisms and it is therefore necessary to protect these latexes during storage and shipment by inhibiting the growth of the microorganisms therein. A number of antimicrobial agents are known in the art for use with latexes. Ideally, such antimicrobial agents should have a high degree of toxicity towards the contaminating microorganisms but should have as little toxicity as possible towards man. Formaldehyde has long been used in latexes as an antimicrobial agent. However, the industry is trending away from the use of formaldehyde as it requires special handling procedures and equipment, and is searching for other effective yet environmentally acceptable antimicrobial agents. A number of other antimicrobial agents for latexes have been developed and used. These include 1,2-benzisothiazolin-3-one, 5-chloro-2-methyl-4-isothiazolin-3-one, 1,2-dibromo-2,4-dicyanobutane, 3,5-dimethyl-tetrahydro-2H-1,3,5-thiadiazine-2-thione, 6-acetoxy-2,4-dimethyl-1,3-dioxane, $\beta$-bromo-$\beta$-nitrostyrene, 2-bromo-2-nitro-1,3-propanediol, and 1-(3-chloroallyl)-2,5,7-triaza-1-azonia-adamantane chloride. In general, these antimicrobial agents are rather costly materials and usually require special handling procedures and equipment for use. Nor do they always provide protection against microorganisms for a sufficient period of time unless larger amounts of the antimicrobial agent are used which undesirably increases the cost of the latex. Additionally, some of these antimicrobial agents can alter the physical properties of polymer latexes, for example by undesirably discolouring latex films on heat aging.

Chlorine dioxide has long been known as a strong oxidizing agent and is used extensively in the pulp and paper industry as a bleaching agent. It has also been used as an antimicrobial agent and odour control agent in water treatment, and as a slimicide in white water systems of paper mills. It is believed that the antimicrobial properties of chlorine dioxide are due to its strong oxidizing properties which disrupt the protein synthesis of the microorganisms.

U.S. Pat. No. 3,092,598 teaches that chlorine dioxide may be used to provide thermal stabilization of latexes of polymers of vinyl chloride or vinylidene chloride. U.S. Pat. No. 3,303,153 teaches that a mixture of chlorine dioxide and a phenolic compound may be used as a polymerization inhibitor in emulsion polymers of vinylidene chloride in order to extend the film-forming life of the emulsion.

Because of the known high reactivity of chlorine dioxide, one skilled in the art would expect that its use as an antimicrobial agent in latexes comprising one or more synthetic polymers would not be viable as the chlorine dioxide would likely react with the polymer particularly when the polymer contains reactive centers such as carbon-carbon double bonds as in polymers derived from diene monomers. Such reactions might degrade the chemical and physical properties of the polymer latex and because the chlorine dioxide is used up in such reactions, the latex would not then be protected against contamination by microorganisms. Surprisingly, it has been found that this is not the case and that latexes comprising one or more synthetic polymers and an antimicrobially effective amount of an antimicrobial agent selected from chlorine dioxide gas, aqueous solutions of chlorine dioxide, and two or more chemical compounds which react upon mixing to form chlorine dioxide have excellent resistance to microbial attack and show no undesirable changes in physical or chemical properties.

It is an object of the present invention to provide an improved method of inhibiting the growth of microorganisms in an aqueous latex comprising one or more synthetic polymers.

It is a further object of the present invention to provide an aqueous latex comprising one or more synthetic polymers which has improved resistance to the growth of microorganisms therein.

Accordingly, the present invention provides an improved method for inhibiting the growth of microorganisms in an aqueous latex comprising one or more synthetic polymers, said process comprising admixing said latex with an antimicrobially effective amount of an antimicrobial agent selected from chlorine dioxide gas, aqueous solutions of chlorine dioxide, and two or more chemical compounds which react upon mixing to form chlorine dioxide.

The present invention further provides an aqueous latex comprising one or more synthetic polymers which has improved resistance to the growth of microorganisms therein wherein said latex additionally comprises an antimicrobially effective amount of chlorine dioxide.

There are many methods known for producing chlorine dioxide. Sodium chlorate is the most important source and chlorine dioxide is generated by treating sodium chlorate with any one of a large variety of reagents. For example, the reagent may be hydrochloric acid optionally in the presence of sodium chloride, buffering ions such as sulfate or phosphate, or catalysts such as $V_2O_5$. In this reaction chlorine gas is produced as a co-product. The reagent may also be sulfuric acid or mixtures of sulfuric and hydrochloric acids; reducing agents such as sulfur dioxide; organic acids such as oxalic, citric or tartaric acid; nitrous acid; nitrogen dioxide; and organic peroxides.

Chlorine dioxide may also be generated by the reaction of sodium chlorite with a variety of reagents including chlorine, hydrochloric acid, sulfuric acid, organic acids and anhydrides, hydrogen peroxide, nitrogen trichloride, acidic formaldehyde and persulfates. In water treatment, the reaction of hypochlorite with chlorite has been used to generate chlorine dioxide.

Because chlorine dioxide is unstable and a potentially explosive gas, methods have been found to provide stable forms of the compound that allow its release on demand. For example, solid chlorine dioxide polyhydrate may be safely handled at low temperature in coated blocks which upon warming generate the gas. Stabilized aqueous solutions of chlorine dioxide with a pH of about 9 and containing about 5 per cent by weight of chlorine dioxide are available commercially. Stabilizing agents such as sodium carbonate or bicarbonate in combination with a peroxide or sodium peroxycarbonate alone are generally used.

Chlorine dioxide generators are also available commercially. These use the reaction between sodium chlorite and chlorine gas as the chlorine dioxide source.

In the process of the present invention, chlorine dioxide gas may be admixed directly with a latex comprising one or more synthetic polymers by simply bubbling the gas into the latex. The gas may be generated by any of the known methods. Alternately in the process of the present invention aqueous solutions of chlorine dioxide, preferably stabilized according to one of the known methods, may be admixed with a latex comprising one or more synthetic polymers by, for example, shaking or stirring.

Two or more compounds which react upon mixing to form chlorine dioxide may also be admixed with a latex comprising one or more synthetic polymers according to the process of the present invention. Such compounds include sodium chlorite with one or more of sodium, potassium or ammonium persulfate optionally in the presence of a stabilizing amount of sodium peroxycarbonate, sodium chlorite with oxalic acid or with acidic formaldehyde, sodium chlorate with an organic acid such as citric, lactic, oxalic or tartaric acid, and sodium chlorate with an organic peroxide such as benzoyl peroxide. Such compounds may be added, preferably as aqueous solutions, simultaneously to the latex or they may be added in sequence. Mixing may be by any convenient method such as by stirring.

An antimicrobially effective amount of the selected antimicrobial agent is admixed with a latex comprising one or more synthetic polymers in the process of the present invention. This amount depends on a number of factors such as the pH of the latex, the number of microorganisms present in the aqueous components used to make the latex, the conditions of manufacture and storage, the type of polymer in the latex and the likelihood of additional contamination occurring during transportation and/or use. The amount also depends upon the type of emulsifier present in the latex as it is known that different emulsifiers promote different rates of growth of microorganisms. As far as it is known, any of the emulsifiers known in the art may be present in the latex of the present invention. A realistic minimum effective amount has been found to be enough of said antimicrobial agent to provide at least about 0.001 part by dry weight of chlorine dioxide in said latex per 100 parts by dry weight of said polymers. A practical upper limit must be cost effective and must also be small enough so as not to disadvantageously alter the properties of the latex. In practice, such an upper limit has been found to be about 1.0 part by weight of chlorine dioxide per 100 parts by dry weight of polymers. Thus, it is preferred that sufficient of the antimicrobial agent be admixed with a latex comprising one or more synthetic polymers to provide from about 0.001 to about 1.0 part by dry weight of chlorine dioxide per 100 parts by dry weight of polymer. More preferably, from about 0.005 to about 0.2 part on the same basis should be provided.

The aqueous latexes comprising one or more synthetic polymers which may be used in connection with the present invention generally contain from about 35 to about 75 percent by dry weight of the synthetic polymers and have a pH of from about 5.5 to about 12.5. Latexes with pH values less than 5.5 are less suitable because strongly acidic conditions produce a slow loss of chlorine dioxide gas from the system thereby reducing the length of time during which the added amount of chlorine dioxide is effective in inhibiting growth of microorganisms in the latex.

Suitable synthetic polymers include polymers prepared by the well known aqueous emulsion free radical polymerization methods and those polymers prepared by other methods and subsequently emulsified in water by methods known in the art. Suitable polymers include homopolymers and copolymers of $C_{4-6}$ conjugated dienes, acrylic polymers, vinyl acetate polymers, vinyl chloride polymers, vinylidene chloride polymers, chloroprene polymers, vinyl pyridine polymers, homopolymers of vinylidene monoaromatic monomers, and copolymers of ethylene and propylene. Preferred polymers include butadiene-styrene copolymers, acrylonitrile-butadiene copolymers, and copolymers of butadiene and styrene with one or more monomers selected from $\alpha,\beta$-unsaturated aldehydes, $\alpha,\beta$-unsaturated carboxylic acids, $C_{1-8}$-alkyl amide derivatives of said acids, $C_{1-4}$-N-alkylol derivatives of said amides, and $C_{1-8}$-alkyl ester derivatives of said acids. Suitable such monomers include acrylic, methacrylic, fumaric, maleic, and itaconic acids, acrolein, hydroxyethyl (meth)acrylate, N-methylolacrylamide and ethylhexylacrylate.

Latexes of the present invention may additionally comprise natural rubber and/or one or more compounding ingredients which are generally used in the art, such as for example, antioxidants, fillers and curing systems.

Latexes of the present invention may be used in any of the many known applications for latexes comprising one or more synthetic polymers, including for example in producing such polymeric products as films, paper coatings, foamed backings for carpets, and can sealants.

It has surprisingly been found that polymeric products such as films made from latexes of the present invention containing no antioxidant and wherein the synthetic polymer is a butadiene-styrene copolymer, develop rubbery properties, such as increased tensile strength, even at room temperature. The reason for this is not understood but it would appear that partial crosslinking occurs both at room temperature and at elevated temperatures.

The following examples illustrate the present invention and are not intended to be limiting.

EXAMPLE 1

The latex used in this example was a carboxylated butadiene-styrene copolymer latex containing 54 percent by dry weight of copolymer having a bound styrene content of 59 percent by weight. The latex had a pH of 6.0 and was known to be heavily contaminated with microorganisms.

The antimicrobial agents used in this and the following examples are listed in Table 1. Compounds A to F and H are examples of antimicrobial agents known in the art for use in synthetic polymer latexes while compound G illustrates the present invention.

400 g samples of the contaminated latex were each placed in 1 liter glass jars equipped with screw top lids. To each of the samples was added one of the compounds A through G using the differing amounts of each compound given in Table 2. The concentration of the antimicrobial agent in the latex is given in parts by dry weight of agent per 100 parts by dry weight of polymer in the latex. After addition of the antimicrobial agent to the latex, the lid of each jar was closed and the contents shaken to ensure adequate mixing. The closed jars were allowed to stand at room temperature. After a period of 19 days, the jars were opened briefly and a further 200 g of the contaminated latex used initially were added to each sample. After the jars were closed, the contents were mixed by shaking and then allowed to stand at room temperature. In a similar manner, a further 100 g of contaminated latex were added to each sample after 145 days.

Each sample was tested for the presence of growing microorganisms in the following manner. After each of the periods of time from the initial mixing of the latex and the antimicrobial agent, as shown in Table 2, the jar was briefly opened and a sterile swab was dipped into the mixture. As quickly as possible to avoid contamination by airborne bacteria, the swab was used to twice streak the surface of a sterile plain blood agar plate and the covering of the plate was then replaced. The jar was also closed and allowed to stand until the next test was run. The streaked agar plate was incubated at 33°±2° C. for 48 hours in an inverted position to prevent the plate and streaks from drying out. After the incubation period, the plate was visually examined for contamination by bacteria colonies on or immediately adjacent to the streaks. The results are shown in Table 2. In this table the amounts of contamination by microorganisms are given by: - for essentially none; S for slight; M for medium; H for heavy. These values were assigned to each sample by visually comparing the contamination of each with an arbitrary standard pictorial scale obtained from samples where actual counts of microorganisms had been made. The symbol — corresponds to less than about 100 colonies of microorganisms per $cm^3$ of the sample, while S corresponds to 100–1000, M to 1000–10,000 and H to greater than 10,000 on the same basis.

The test conditions used in this and the other Examples which follow were designed to be much more severe than conditions found in normal practice. The results show that chlorine dioxide is as good as any of the other antimicrobial agents tested and better than some of them. It performs well under static conditions and also under conditions of further added contamination. No significant change in pH was noted in any of the samples over the length of the test.

TABLE 1

| ANTIMICROBIAL AGENT | CHEMICAL NAME |
|---|---|
| A | 1,2-benzisothiazolin-3-one |
| B | 5-chloro-2-methyl-4-isothiazolin-3-one |
| C | 1,2-dibromo-2,4-dicyanobutane |
| D | 3,5-dimethyltetrahydro-2H—1,3,5-thiadiazine-2-thione |
| E | 6-acetoxy-2,4-dimethyl-1,3-dioxane |
| F | β-bromo-β-nitrostyrene |
| G | chlorine dioxide ($ClO_2$) as a stabilized 5 percent aqueous solution sold under the tradename ANTHIUM DIOXCIDE by International Dioxcide Inc. |
| H | formaldehyde |

TABLE 2

| ANTIMICROBIAL AGENT | | | CONTAMINATION OBSERVED AFTER (No. of Days) | | | | | | |
|---|---|---|---|---|---|---|---|---|---|
| | CONCENTRATION | | | | | | | | |
| IDENTITY | DAYS 1–18 | DAYS 19–144 | DAYS 145–178 | 2 | 13 | 23 | 42 | 123 | 150 | 178 |
| A | 0.023 | 0.015 | 0.013 | — | — | — | — | — | — | — |
| | 0.033 | 0.022 | 0.019 | — | — | — | — | — | — | — |
| | 0.05 | 0.033 | 0.029 | — | — | — | — | — | — | — |
| | 0.066 | 0.044 | 0.038 | — | — | — | — | — | — | — |
| B | 0.013 | 0.009 | 0.007 | — | — | — | — | — | S | — |
| | 0.023 | 0.015 | 0.013 | — | — | — | — | — | S | — |
| | 0.033 | 0.022 | 0.019 | — | — | — | — | — | — | — |
| | 0.05 | 0.033 | 0.029 | — | — | — | — | — | S | — |
| | 0.066 | 0.044 | 0.038 | — | — | — | — | — | S | — |
| C | 0.013 | 0.009 | 0.007 | — | — | — | — | — | M | — |
| | 0.023 | 0.015 | 0.013 | S | — | — | — | — | H | — |
| | 0.033 | 0.022 | 0.019 | — | — | — | — | — | H | — |
| | 0.05 | 0.033 | 0.029 | — | — | — | — | — | H | S |
| | 0.066 | 0.044 | 0.038 | S | — | — | — | — | H | S |
| D | 0.013 | 0.009 | 0.007 | — | — | — | — | — | H | S |
| | 0.023 | 0.015 | 0.013 | — | — | — | — | — | H | — |
| | 0.033 | 0.022 | 0.019 | — | — | — | — | — | H | H |
| | 0.05 | 0.033 | 0.029 | — | — | — | — | — | H | H |
| | 0.066 | 0.044 | 0.038 | — | — | — | — | — | H | H |
| E | 0.013 | 0.009 | 0.007 | H | — | H | — | — | H | H |
| | 0.023 | 0.015 | 0.013 | H | — | H | — | — | H | H |
| | 0.033 | 0.022 | 0.019 | H | — | M | — | — | H | H |
| | 0.05 | 0.033 | 0.029 | M | — | S | — | — | H | H |
| | 0.066 | 0.044 | 0.038 | S | — | — | — | — | H | H |
| F | 0.013 | 0.009 | 0.007 | — | — | M | — | — | H | H |
| | 0.023 | 0.015 | 0.013 | — | — | — | — | — | H | H |
| | 0.033 | 0.022 | 0.019 | — | — | — | — | — | H | H |

TABLE 2-continued

| IDENTITY | ANTIMICROBIAL AGENT CONCENTRATION | | | CONTAMINATION OBSERVED AFTER (No. of Days) | | | | | | |
|---|---|---|---|---|---|---|---|---|---|---|
| | DAYS 1-18 | DAYS 19-144 | DAYS 145-178 | 2 | 13 | 23 | 42 | 123 | 150 | 178 |
| | 0.05 | 0.033 | 0.029 | — | — | — | — | — | H | H |
| | 0.066 | 0.044 | 0.038 | — | — | — | — | — | H | H |
| G | 0.013 | 0.009 | 0.007 | — | — | H | — | H | H | H |
| | 0.023 | 0.015 | 0.013 | — | — | H | — | M | H | H |
| | 0.033 | 0.022 | 0.019 | — | — | M | — | — | H | H |
| | 0.05 | 0.033 | 0.029 | — | — | — | — | — | S | H |
| | 0.066 | 0.044 | 0.038 | — | — | — | — | — | S | M |
| | 0.099 | 0.067 | 0.057 | — | — | — | — | — | — | — |
| | 0.198 | 0.132 | 0.113 | — | — | — | — | — | — | — |

EXAMPLE 2

In this example, the procedure used was the same as that used in Example 1 except that the pH of the contaminated latex was adjusted to 8.8 with ammonia prior to the addition of the antimicrobial agent. Results are given in Table 3 and are very similar to those obtained in Example 1.

TABLE 3

| IDENTITY | ANTIMICROBIAL AGENT CONCENTRATION | | | CONTAMINATION OBSERVED AFTER (No. of Days) | | | | | | |
|---|---|---|---|---|---|---|---|---|---|---|
| | DAYS 1-18 | DAYS 19-144 | DAYS 145-178 | 2 | 13 | 23 | 42 | 123 | 150 | 178 |
| A | 0.0132 | 0.009 | 0.007 | — | — | — | — | — | S | — |
| | 0.0198 | 0.0132 | 0.011 | — | — | — | — | — | — | — |
| | 0.0264 | 0.0176 | 0.015 | — | — | — | — | — | — | — |
| | 0.033 | 0.022 | 0.019 | — | — | — | — | — | S | — |
| B | 0.007 | 0.0043 | 0.004 | — | — | — | — | — | — | — |
| | 0.0132 | 0.009 | 0.007 | — | — | — | — | — | — | S |
| | 0.0198 | 0.0132 | 0.011 | — | — | — | — | — | S | — |
| | 0.0264 | 0.0176 | 0.015 | — | — | — | — | — | — | — |
| | 0.033 | 0.022 | 0.019 | — | — | — | — | — | — | — |
| C | 0.007 | 0.0043 | 0.004 | S | — | H | H | H | H | H |
| | 0.0132 | 0.009 | 0.007 | S | — | H | H | H | H | H |
| | 0.0198 | 0.0132 | 0.011 | S | — | H | H | H | H | H |
| | 0.0264 | 0.0176 | 0.015 | S | — | H | H | H | H | H |
| | 0.033 | 0.022 | 0.019 | S | — | H | H | H | H | H |
| D | 0.007 | 0.0043 | 0.004 | S | — | H | H | H | H | H |
| | 0.0132 | 0.009 | 0.007 | S | — | — | H | H | M | H |
| | 0.0198 | 0.0132 | 0.011 | S | — | H | H | H | M | H |
| | 0.0297 | 0.0198 | 0.017 | S | — | — | H | H | M | M |
| | 0.0396 | 0.0264 | 0.023 | — | — | — | H | H | H | S |
| E | 0.007 | 0.0043 | 0.004 | S | H | H | H | H | H | H |
| | 0.0132 | 0.009 | 0.007 | S | H | H | H | H | H | H |
| | 0.0198 | 0.0132 | 0.011 | S | M | H | H | H | H | H |
| | 0.0297 | 0.0198 | 0.017 | S | — | H | H | H | H | H |
| | 0.0396 | 0.0264 | 0.023 | S | — | H | H | H | H | H |
| F | 0.007 | 0.0043 | 0.004 | S | — | H | H | H | H | H |
| | 0.0132 | 0.009 | 0.007 | — | — | H | H | H | H | H |
| | 0.0198 | 0.0132 | 0.011 | — | — | H | H | H | H | H |
| | 0.0297 | 0.0198 | 0.017 | — | — | H | H | H | H | H |
| | 0.0396 | 0.0264 | 0.023 | — | — | H | H | H | H | H |
| G | 0.0264 | 0.0176 | 0.015 | — | — | H | H | H | H | H |
| | 0.0396 | 0.0264 | 0.023 | — | — | — | — | — | — | S |
| | 0.0528 | 0.0352 | 0.03 | — | — | — | — | — | — | M |
| | 0.066 | 0.044 | 0.038 | — | — | — | — | — | S | H |
| | 0.099 | 0.066 | 0.057 | — | — | — | — | — | S | M |
| | 0.198 | 0.132 | 0.113 | — | — | — | — | — | — | — |

EXAMPLE 3

The procedure used in this example was that of Example 1 with the following exceptions. The latex used was a contaminated butadiene-styrene copolymer latex containing 70 percent by dry weight of copolymer having a bound styrene content of 23 percent by weight. The starting pH was 10.0 and the pH of each of the samples was adjusted on day 3 with 10 percent aqueous potassium hydroxide or carbon dioxide as shown in Table 4. On day 47, each sample was contaminated with 100 g of the contaminated latex used in Example 1 (pH adjusted to 9.0). Results are given in Table 4. Chlorine dioxide is shown to be comparable in all respects with the other agents tested. pH measurements at days 29 and 140 showed that no significant change in pH occurred during this period in any of the samples tested.

TABLE 4

| ANTIMICROBIAL AGENT | | | pH | | | CONTAMINATION OBSERVED AFTER | | | |
|---|---|---|---|---|---|---|---|---|---|
| | CONCENTRATION | | | | | | | | |
| | DAYS | DAYS | DAY | DAY | DAY | (No. of days) | | | |
| IDENTITY | 1–46 | 47–144 | 3 | 29 | 140 | 4 | 26 | 53 | 144 |
| D | 0.04 | 0.032 | 11.5 | 10.9 | 10.1 | — | — | — | — |
| | | | 11.1 | 11.4 | 10.1 | — | — | — | — |
| | | | 10.5 | 10.4 | 9.9 | — | — | — | — |
| | | | 10.0 | 10.0 | 9.7 | — | — | — | — |
| | | | 9.5 | 9.6 | 9.5 | — | — | — | — |
| | | | 9.0 | 9.1 | 9.4 | — | — | H | — |
| G | 0.02 | 0.016 | 11.5 | 11.1 | 9.9 | — | — | — | — |
| | | | 11.0 | 10.9 | 10.0 | — | — | — | — |
| | | | 10.5 | 10.5 | 9.8 | — | — | — | — |
| | | | 9.9 | 9.7 | 9.6 | — | — | — | — |
| | | | 9.5 | 9.1 | 9.3 | — | — | — | — |
| | | | 9.0 | 8.7 | 8.8 | — | — | H | M |
| G | 0.04 | 0.032 | 11.5 | 11.1 | 9.9 | — | — | — | — |
| | | | 11.0 | 10.9 | 9.9 | — | — | — | — |
| | | | 10.6 | 10.6 | 9.8 | — | — | — | — |
| | | | 10.0 | 9.9 | 9.7 | — | — | — | — |
| | | | 9.5 | 9.5 | 9.5 | — | — | — | — |
| | | | 9.0 | 9.5 | 9.3 | — | — | — | — |
| G | 0.06 | 0.048 | 11.5 | 11.2 | 10.0 | — | — | — | — |
| | | | 11.0 | 10.8 | 9.9 | — | — | — | — |
| | | | 10.5 | 10.4 | 9.8 | — | — | — | — |
| | | | 10.0 | 10.8 | 9.7 | — | — | — | — |
| | | | 9.5 | 9.5 | 9.5 | — | — | — | — |
| | | | 9.0 | 9.2 | 9.3 | — | — | — | — |
| G | 0.08 | 0.064 | 11.5 | 10.9 | 9.9 | — | — | — | — |
| | | | 11.0 | 10.8 | 9.8 | — | — | — | — |
| | | | 10.6 | 10.4 | 9.7 | — | — | — | — |
| | | | 10.0 | 10.1 | 9.5 | — | — | — | — |
| | | | 9.5 | 9.5 | 9.4 | — | — | — | — |
| | | | 9.0 | 9.2 | 9.3 | — | — | — | — |
| H | 0.03 | 0.024 | 11.5 | 11.5 | 10.1 | — | — | — | — |
| | | | 11.0 | 11.2 | 9.9 | — | — | — | — |
| | | | 10.6 | 10.8 | 9.9 | — | — | — | — |
| | | | 10.0 | 10.0 | 9.6 | — | — | — | — |
| | | | 9.5 | 9.7 | 9.5 | — | — | — | — |
| | | | 9.0 | 9.2 | 9.4 | — | — | — | — |

EXAMPLE 4

The procedure used in this example was that of Example 1 with the following exceptions. The latex used was a carboxylated styrene-butadiene copolymer latex containing 55.6 percent by dry weight of copolymer having a bound styrene content of 58 percent by weight. The latex ph was 6.45 and the latex was much more heavily contaminated with microorganisms than the latexes used in Examples 1–3. A variety of antimicrobial agents were used to compare various sources for chlorine dioxide.

Runs 1 and 2 are examples of the use of chlorine dioxide gas as the antimicrobial agent. Sufficient chlorine dioxide gas was bubbled into the latex to give the concentration shown in Table 5.

Runs 4 to 12 are examples of the use of an aqueous solution of chlorine dioxide as the antimicrobial agent. In runs 3 and 4, commercially available agent G from Table 1 was used. In runs 5 and 6, chlorine dioxide gas was dissolved in 100 ml of an aqueous solution of sodium peroxycarbonate (10 g) and sodium chloride (3.44 g) to give a 5 percent by weight solution of chlorine dioxide with a pH of 8.85. Runs 7 and 8 were the same as runs 5 and 6 except that the sodium chloride was omitted. In runs 9 and 10, chlorine dioxide gas was dissolved in 100 ml of an aqueous solution containing 13 g of sodium peroxycarbonate to give a 7.4 percent by weight solution of chlorine dioxide with a pH of 8.8. In runs 11 and 12, 8 g of sodium chlorite and 11 g of potassium persulfate were simultaneously added to 100 ml of a 10 percent by weight aqueous solution of sodium peroxycarbonate using an ice bath to keep the solution at 20°–25° C. The final pH was 8.4. In each run, sufficient of the aqueous solution was added to the latex to give the concentration of chlorine dioxide shown in Table 5.

Runs 13 to 22 are examples of the use of chemical compounds which react upon mixing to form chlorine dioxide. In runs 13 and 14, 0.355 ml of a 20 percent by weight aqueous solution of sodium chlorite and 2.65 ml of a 4 percent by weight aqueous solution of potassium persulfate were added almost simultaneously with stirring to the latex sample. Runs 15 and 16 were the same as runs 13 and 14 except that 0.244 ml of a 40 percent by weight aqueous solution of ammonium persulfate was used in place of the potassium persulfate solution. Runs 17 and 18 were the same as runs 15 and 16 except that the amounts of the sodium chlorite and ammonium persulfate solutions were doubled. Runs 19 and 20 were the same as runs 15 and 16 except that the amounts of the sodium chlorite and potassium persulfate solutions were tripled. Runs 21 and 22 were the same as runs 15 and 16 except that the amounts of the added solutions were quadrupled.

Results are given in Table 5. The concentration of chlorine dioxide is given in parts by dry weight added or capable of being generated by the reacting chemical compounds, per 100 parts by weight of polymer in the latex. In the table, nm means that the contamination was not measured.

TABLE 5

| Run No. | ClO$_2$ Source | ClO$_2$ Concentration | Contamination (After No. of Days) | | | |
|---|---|---|---|---|---|---|
| | | | 3 | 8 | 19 | 33 |
| 1 | ClO$_2$ gas | 0.023 | — | — | — | — |
| 2 | as 1 | 0.11 | — | — | — | — |
| 3 | G (Table 1) | 0.023 | M | H | H | H |
| 4 | as 3 | 0.045 | S | M | H | H |
| 5 | ClO$_2$ in sodium peroxycarbonate/NaCl solution | 0.023 | H | H | H | H |
| 6 | as 5 | 0.045 | S | H | H | H |
| 7 | ClO$_2$ in sodium peroxycarbonate solution | 0.023 | H | H | H | H |
| 8 | as 7 | 0.045 | S | M | H | nm |
| 9 | as 7 | 0.023 | M | H | H | nm |
| 10 | as 7 | 0.045 | S | H | H | nm |
| 11 | NaClO$_2$ + K$_2$S$_2$O$_8$ in sodium peroxycarbonate solution | 0.023 | H | H | H | nm |
| 12 | as 11 | 0.045 | — | H | H | nm |
| 13 | NaClO$_2$ + K$_2$S$_2$O$_8$ | 0.024 | — | — | — | — |
| 14 | as 12 | 0.048 | — | — | — | — |
| 15 | NaClO$_2$ + (NH$_4$)$_2$S$_2$O$_8$ | 0.024 | —* | nm | nm | nm |
| 16 | as 15 | 0.024 | —* | nm | nm | nm |
| 17 | as 15 | 0.048 | — | nm | nm | nm |
| 18 | as 15 | 0.048 | — | nm | nm | nm |
| 19 | as 15 | 0.072 | — | — | nm | nm |
| 20 | as 15 | 0.072 | — | — | nm | nm |
| 21 | as 15 | 0.096 | — | — | nm | nm |
| 22 | as 15 | 0.096 | — | — | nm | nm |

*Contamination after 2 days

EXAMPLE 5

This example demonstrates that the use of chlorine dioxide antimicrobial agent in a latex of a synthetic polymer produces no undesirable changes in the properties of a film formed from the latex.

Two latexes were tested. Latex A was a butadiene-styrene copolymer latex containing 70 percent by weight of copolymer with a bound styrene content of 23 percent by weight. Latex B was a carboxylated butadiene-styrene copolymer latex containing 55.6 percent by dry weight of copolymer with a bound styrene content of 58 percent by weight.

In each run, the latex was thickened by the addition of a thickening agent to allow for film formation. Sufficient amounts of a 20 percent by weight aqueous solution of sodium chlorite and a 40 percent by weight aqueous solution of ammonium persulfate were first added to the latex to provide the concentration of generated chlorine dioxide shown in Tables 6 and 7 given as parts by dry weight of chlorine dioxide per 100 parts by dry weight of polymer in the latex. The latex was then stored at room temperature for 24 hours and then thickened and spread upon a TEFLON ® board to a thickness of about 0.06 cm and allowed to dry. The dried film was then peeled off the board and cut into two equal pieces. The first was tested as is while the second was first heated in an oven at 100° C. for 30 minutes and then cooled to room temperature and tested. Modulus, tensile strength and elongation were determined using ASTM dumbbells cut from the films. Results are shown in Table 6 for samples not heated in the oven while Table 7 shows results for the samples which were heated in the oven. Partial crosslinking of the latex films obtained from Latex A apparently occured even at room temperature when chlorine doxide was present in the latex.

Control runs were made in a similar manner with no chlorine dioxide antimicrobial agent present.

TABLE 6

| Latex | ClO$_2$ Concentration | Elongation (%) | Modulus (kg/cm$^2$) | | | Tensile Strength (kg/cm$^2$) |
|---|---|---|---|---|---|---|
| | | | 100% | 300% | 500% | |
| A | 0 (control) | 310 | 5.1 | 1.2 | — | 0.25 |
| A | 0.018 | 980 | 5.8 | 6.7 | 7.4 | 13.5 |
| A | 0.036 | 890 | 5.6 | 7.7 | 8.7 | 17.6 |
| B | 0 (control) | 745 | 5.2 | 7.2 | 11.9 | 29.3 |
| B | 0.024 | 735 | 5.0 | 7.0 | 11.5 | 29.2 |
| B | 0.048 | 705 | 5.5 | 7.4 | 12.2 | 28.6 |

TABLE 7

| Latex | ClO$_2$ Concentration | Elongation (%) | Modulus (kg/cm$^2$) | | | Tensile Strength (kg/cm$^2$) |
|---|---|---|---|---|---|---|
| | | | 100% | 300% | 500% | |
| A | 0 (control) | 345 | 5.6 | 3.9 | — | 2.6 |
| A | 0.018 | 1010 | 5.9 | 6.2 | 6.7 | 11.3 |
| A | 0.036 | 1070 | 5.5 | 6.5 | 7.3 | 16.3 |
| B | 0 (control) | 685 | 6.0 | 8.1 | 13.9 | 30.4 |
| B | 0.024 | 690 | 6.1 | 8.9 | 15.4 | 37.5 |
| B | 0.048 | 680 | 6.1 | 8.3 | 14.2 | 30.8 |

EXAMPLE 6

This example demonstrates that the use of chlorine dioxide antimicrobial agent in a latex of a synthetic polymer produces no undesirable changes in the properties of latex foam rubber formed from the latex.

Latex A of Example 5 was used to produce both gelled and no-gel foams. Two samples of each type were prepared, one containing no chlorine dioxide as a control and a second containing sufficient sodium chlorite and ammonium persulfate to generate 0.048 parts by weight of chlorine dioxide per 100 parts by weight of polymer in the latex.

The gelled foam samples were produced as follows. The ingredients listed in Table 8 were thoroughly mixed. The mixture was then foamed in a Hobart mixer and 3.0 parts by dry weight of sodium silicofluoride were slowly added to the foam with continuous foaming. The mixture was then refined for one minute and then poured onto a jute substrate, spread to a thickness of about 0.6 cm and cured in an oven at 135° C. for 25 minutes. Properties were measured according to standard well-known methods and results are shown in Table 10.

The no-gel foam samples were produced as follows. The ingredients listed in Table 9 were thoroughly mixed. This mixture was foamed in a Hobart mixer, refined for 5 minutes, poured onto a jute substrate, spread to a thickness of about 0.6 cm and cured in an oven at 135° C. for 20 minutes. Physical properties are shown in Table 10.

None of the foams showed any signs of cracking after aging at 135° C. for 72 hours. The properties of the foams made from the latex of the invention are equivalent in every way to the control foams.

TABLE 8

| Ingredient | Parts by dry weight | |
|---|---|---|
| | Control | Invention |
| Latex | 100.0 | 100.0 |
| Potassium salt of rosin acid | 2.0 | 2.0 |
| Ammonium hydroxide | 0.1 | 0.1 |
| Sodium chlorite | — | 0.05 |
| Ammonium persulfate | — | 0.064 |
| 3:1 parts by weight mixture of zinc oxide and diphenylguanidine ball milled for 2 hours | 3.4 | 3.4 |
| Water-washed aluminum silicate | 140.0 | 140.0 |
| Curing system | | |
| Sulfur | 1.65 | 1.65 |
| Zinc oxide | 1.25 | 1.25 |
| Ethyl zimate | 1.00 | 1.00 |
| Zinc salt of mercaptobenzothiazole | 1.25 | 1.25 |
| Antioxidant - diphenylamine acetone reaction product | 0.45 | 0.45 |
| Antioxidant - polymeric bindered phenol | 0.30 | 0.30 |

TABLE 9

| Ingredient | Parts by dry weight | |
|---|---|---|
| | Control | Invention |
| Latex | 100.0 | 100.0 |
| Disodium N—octadecyl sulfosuccinamate | 4.0 | 4.0 |
| Sodium hexametaphosphate | 0.5 | 0.5 |
| Potassium hydroxide | 0.2 | 0.2 |
| Sodium chlorite | — | 0.05 |
| Ammonium persulfate | — | 0.064 |
| Calcium carbonate | 150.0 | 150.0 |
| Curing system | | |
| same as for gelled foam, total 5.9 parts | 5.9 | 5.9 |

TABLE 10

| Foam | Tensile strength (kg/cm$^2$) | Elongation (%) | Delamination (kg/cm$^2$) | Compression Resistance (kg/cm$^2$) | Compression Set (%) |
|---|---|---|---|---|---|
| Gelled (control) | 0.61 | 225 | 0.11 | 0.14 | 13.6 |
| Gelled (invention) | 0.69 | 270 | 0.13 | 0.16 | 18.8 |
| No-gel (control) | 0.60 | 341 | 0.11 | 0.18 | 6.8 |
| No-gel (invention) | 0.58 | 333 | 0.10 | 0.20 | 7.0 |

What is claimed is:

1. A latex having improved resistance to the growth of bacteria comprising from about 35 to 75 parts by weight of one or more polymers selected from the group:

homopolymers of $C_{4-6}$ conjugated diolefins, chloroprene polymers, vinyl pyridine polymers, homopolymers of vinylidene monoaromatic monomers, copolymers of ethylene and propylene, copolymers of acrylonitrile and butadiene; or copolymers of butadiene and styrene, copolymers of butadiene and styrene containing one or more monomers selected from the group alpha,beta ethylenically unsaturated carboxylic acids, amide derivatives of alpha,beta ethylenically unsaturated acids which are unsubstituted or substituted at the nitrogen atom by a $C_{1-8}$ alkyl or a $C_{1-4}$ alkanol radical, or a $C_{1-8}$ alkyl ester of an alpha,beta ethylenically unsaturated carboxylic acid; and per 100 parts by weight to polymer solids in said latex a sufficient amount of an agent selected from the group:

chlorine dioxide gas, aqueous solutions of chlorine dioxide, a mixture of an alkali metal chlorate and a mineral acid, a mixture of an alkali metal chlorate and an organic acid, or an organic anhydride, a mixture of an alkali metal chlorate and an organic peroxide or hydrogen peroxide, a mixture of an alkali metal chlorate and a reducing agent, a mixture of an alkali metal chlorite and mineral acid, a mixture of an alkali metal chlorite and an organic acid or an organic anhydride, a mixture of an alkali metal chlorite and an organic peroxide or hydrogen peroxide, a mixture of an alkali metal chlorite and a reducing agent or a mixture of an alkali metal chlorite and chlorine, to provide from about 0.005 to about 0.2 parts by weight of chlorine dioxide per 100 parts by weight of polymer solids.

2. A latex according to claim 1 wherein said polymer is a copolymer of a $C_{4-6}$ conjugated diene selected from butadiene-styrene copolymers, butadiene-acrylonitrile copolymers or copolymers of butadiene and styrene with one or more monomers selected from alpha,beta unsaturated aldehydes, alpha,beta unsaturated carboxylic acids, amide derivatives of alpha,beta ethylenically unsaturated acids which are unsubstituted or substituted at the nitrogen atom by a $C_{1-8}$ alkyl or a $C_{1-4}$ alkanol radical, or a $C_{1-8}$ alkyl ester of an alpha,beta ethylenically unsaturated carboxylic acid.

3. A latex according to claim 2 having a pH greater than 5.5.

4. A method for inhibiting the growth of microorganisms in an aqueous latex of one or more polymers selected from the group:

homopolymers of $C_{4-6}$ conjugated diolefins, chloroprene polymers, vinyl pyridine polymers, homopolymers of vinylidene monoaromatic monomers, copolymers of ethylene and propylene, copolymers of acrylonitrile and butadiene or copolymers of butadiene and styrene, copolymers of butadiene and styrene containing one or more monomers selected from the group alpha-beta ethylenically unsaturated aldehydes, alpha-beta ethylenically unsaturated carboxylic acids, amide derivatives of alpha-beta ethylenically unsaturated acids which are unsubstituted or substituted at the nitrogen atom by a $C_{1-8}$ alkyl or a $C_{1-4}$ alkanol radical, or a $C_{1-8}$ alkyl ester of an alpha-beta ethylenically unsaturated carboxylic acid;

which comprises adding to said latex an agent selected from the group chlorine dioxide gas, aqueous solutions of chlorine dioxide, a mixture of an alkali metal chlorate and a mineral acid, a mixture of an alkali metal chlorate and an organic acid, or an organic anhydride, a mixture of an alkali metal chlorate and an organic peroxide or hydrogen peroxide, a mixture of an alkali metal chlorate and a reducing agent, a mixture of an alkali metal chlorite and mineral acid, a mixture of an alkali metal chlorite and an organic acid or an organic anhydride, a mixture of an alkali metal chlorite and an organic peroxide or hydrogen peroxide, a mixture of an alkali metal chlorite and a reducing agent or a mixture of an alkali metal chlorite and chlorine, in an amount sufficient to provide from about 0.001 to about 1.0 parts by dry weight of chlorine dioxide per 100 parts by weight of polymer in the latex.

5. The method according to claim 4 wherein said polymer is a copolymer of a $C_{4-6}$ conjugated diene selected from butadiene-styrene copolymers, butadiene-acrylonitrile copolymers, or copolymers of butadiene and styrene with one or more monomers selected from alpha,beta-unsaturated aldehydes, alpha,beta-unsaturated carboxylic acids, amide derivatives of alpha,beta ethylenically unsaturated acids which are unsubstituted or substituted at the nitrogen atom by a $C_{1-8}$ alkyl or a $C_{1-4}$ alkanol radical, or a $C_{1-8}$ alkyl ester of an alpha,beta ethylenically unsaturated carboxylic acid.

6. A method according to claim 5 wherein said agent is chlorine dioxide gas.

7. A method according to claim 5 wherein said agent is an aqueous solution of chlorine dioxide gas.

8. A method according to claim 5 wherein said agent is a mixture of sodium chlorate and a mineral acid selected from the group sulphuric acid, hydrochloric acid or a mixture of sulphuric acid and hydrochloric acid.

9. A method according to claim 5 wherein said agent is a mixture of sodium chlorate and an organic acid selected from the group citric acid, lactic acid, oxalic acid, or tartaric acid.

10. A method according to claim 5 wherein said agent is a mixture of sodium chlorate and a reducing agent selected from the group sulphur dioxide, sodium persulphate, potassium persulphate, ammonium persulphate or a mixture thereof.

11. A method according to claim 5 wherein said agent is a mixture of sodium chlorate and a peroxide selected from the group hydrogen peroxide, or benzoyl peroxide.

12. A method according to claim 5 wherein said agent is a mixture of sodium chlorate and an organic acid selected from the group citric acid, lactic acid, oxalic acid, or tartaric acid.

13. A method according to claim 5 wherein said agent is a mixture of sodium chlorate and a reducing agent selected from the group sodium persulphate, potassium persulphate, ammonium persulphate or a mixture thereof.

14. A method according to claim 5 wherein said agent is a mixture of sodium chlorate and a peroxide selected from the group hydrogen peroxide, or benzoyl peroxide.

15. A method according to claim 13 wherein said agent is stabilized with a stabilizer selected from the group comprising an alkali metal peroxycarbonate.

16. A method according to claim 5 wherein said agent is a mixture of sodium chlorite and chlorine.

17. A method according to claim 5 wherein said agent comprises one or more members of the group sodium, or potassium chlorite and one or more members from the group sodium, potassium, or ammonium persulfate, in an amount to provide from 0.005 to 0.2 parts by dry weight of chlorine dioxide per 100 parts by weight of polymer in said latex.

* * * * *